United States Patent [19]
Rao

[11] Patent Number: 5,196,615
[45] Date of Patent: Mar. 23, 1993

[54] CATALYZED HYDROFLUORINATION HALOGENATED ALKANES

[75] Inventor: V. N. Mallikarjuna Rao, Wilmington, Del.

[73] Assignee: E. I. Du Pont de Nemours and Company, Wilmington, Del.

[21] Appl. No.: 570,952

[22] Filed: Aug. 22, 1990

Related U.S. Application Data

[63] Continuation of Ser. No. 365,655, Jun. 16, 1989, abandoned, which is a continuation-in-part of Ser. No. 210,556, Jun. 23, 1988, abandoned.

[51] Int. Cl.$^5$ ............................................. C07C 17/08
[52] U.S. Cl. ...................................................... 570/168
[58] Field of Search ................................. 570/168, 166

[56] References Cited

FOREIGN PATENT DOCUMENTS 0256146 2/1988 European Pat. Off. .
52-103392 8/1977 Japan .

OTHER PUBLICATIONS

Feiring, A. E. J of Flourine Chem. 13 pp. 7–18 (1979).

Primary Examiner—Alan Siegel

[57] ABSTRACT

Process for the preparation of fluorinated alkanes by contacting halogenated alkanes with HF in the presence of $TaCl_5$ or $TaBr_5$.

8 Claims, No Drawings

CATALYZED HYDROFLUORINATION HALOGENATED ALKANES

This application is a continuation of application Ser. No. 07/365,655 filed Jun. 16, 1989 now abandoned, which is a continuation-in-part of U.S. application Ser. No. 07/210,556 filed Jun. 23, 1988 now abandoned.

FIELD OF INVENTION

Process for the preparation of fluorinated alkanes by contacting halogenated alkanes with hydrogen fluoride in the presence of $TaCl_5$ or $TaBr_5$.

BACKGROUND OF INVENTION

JP 52/103392 discloses and claims a catalyst for fluorinating a halogenated hydrocarbon which is obtained by mixing tantalum (V) halide with an antimony halide catalyst which consists of antimony (V) halide or a mixture consisting of said antimony halide and antimony (III) halide. If the resulting fluorination catalyst is used, the fluorination of a halogenated hydrocarbon can be accelerated more effectively than in a case when an unmodified antimony halide catalyst is used, and the production rate of the objective fluorinated compound per unit catalyst (weight) can be maximized. The patent clearly shows in Comparative Example 2 that tantalum pentachloride alone is ineffective as a fluorine exchange catalyst for the conversion of 1,1,1,2-tetrachlorodifluoroethane to 1,1,2-trichlorotrifluoroethane.

The need for environmentally suitable fluorocarbons for use as refrigerants, blowing agents and solvents has grown and spurred investigation of economically attractive routes to their production. The fluorinated alkanes produced by the process of this invention are useful as refrigerants, blowing agents or solvents per se or can be utilized as intermediates for the production of other halogenated alkanes which fill the same needs.

SUMMARY OF THE INVENTION

This invention is a process for the preparation of fluorinated alkanes by contacting at a temperature of about 0° C. to about 185° C. under substantially anhydrous conditions, one molar equivalent of a starting material selected from halogenated alkanes of the following formulas $$R^1R^2R^3 \text{ and } R^5R^6R^7R^8C$$

wherein
$R^1$, $R^2$, $R^3$, $R^4$, and $C_xZ_{2x=1}$, wherein Z is H, F, Br, or Cl and x=0 to 10 with the proviso that at least one of $R^1$, $R^2$, $R^3$, or $R^4$ be Cl or Br or contain Cl or Br;
$R^5$ and $R^6$ taken together are —$(CH_2)_n$— wherein n is an integer from 2 to 7, wherein $R^7$ and $R^8$ are $C_xZ_{2x-1}$, wherein Z is H, F, Br, or Cl and x=0 to 10, with the proviso that at least $R^7$ or $R^8$ is Cl or contains Cl or Br, with HF in the presence of at least one catalyst selected from tantalum pentachloride and tantalum pentabromide to produce a fluorinated alkane.

DETAILS OF THE INVENTION

The resulting fluorinated alkane produced in accordance with the invention has one or more fluorine atoms over and above the number of fluorine atoms originally present in the halogenated alkane.

The halogenated alkane starting materials of the invention do not substantially react with hydrogen fluoride alone under the conditions of temperature and pressure used in this invention and require the presence of added catalyst, specifically tantalum pentachloride ($TaCl_5$) or tantalum pentabromide ($TaBr_5$). It is preferred that the $TaCl_5$ or $TaBr_5$ be used in an amount from 0.001 to about 5 moles, more preferably 0.001 to 0.250 mole per mole of starting halogenated alkanes for reasons of economy and effectiveness. $TaCl_5$ is the preferred catalyst. The catalyst is a commercially available crystalline solid and can be used alone or on a support, such as carbon.

The preferred halogenated alkanes of the formula $R^1R^2R^3R^4C$ are wherein x=0 to 3, and more preferably from 0 to 1. n is preferably from 4 to 6. In a particularly preferred embodiment $R^1=C_xZ_{2x=1}$, wherein x=1 and $R^2$, $R^3$, and $R^4$ are selected from H, F, Cl and Br. In addition to the proviso that at least one of $R^1$, $R^2$, R3 and $R^4$ be Cl or Br, or contain Cl or Br. It is also preferred that at least one of $R^1$, $R^2$, $R^3$ and $R^4$ be H. The specifically preferred halogenated alkanes are selected from $CHCl_3$, $CH_2Cl_2$, $CHCl_2CHCl_2$, $CH_2ClCCl_3$, $CCl_2FCH_2Cl$, $CClF_2CH_2Cl$, $CF_3CHCl_2$, $CHClF_2$ and $CHCl_2F$.

The reaction can be carried out in the pressures or under constant pressure ranging from atmospheric to superatmospheric. Both the liquid phase and vapor phase processes include batch, semicontinuous and continuous modes of operation.

The reaction can be carried out at from about 0° C. to about 185° C. The preferred temperature is about 35° C. to about 175° C.

Anhydrous or substantially anhydrous conditions means that water, which is detrimental to the reaction, should be excluded as much as possible from the reaction zone. The HF which is commercially available as anhydrous grade can be used in the reaction directly. It is preferred that 1 to 30 molar equivalents of HF be utilized. Exclusion of moisture from the reaction vessel by means of appropriate moisture traps or other means is a routine procedure and is well known in the art.

The reaction vessel is constructed from materials which are resistant to the action of "Hastelloy" and "Inconel".

The liquid phase reactions are conducted by introducing the reagents in any order into the reaction vessel. Generally, the $TaCl_5$ or $TaBr_5$ and starting halogenated alkane are placed in the reaction vessel which is then cooled, and the required amount of hydrogen fluoride is condensed in the vessel. The vessel may be evacuated prior to the introduction of hydrogen fluoride and cooled in Dry Ice or liquid nitrogen to facilitate addition of the hydrogen fluoride. The contents of the vessel are raised to the appropriate reaction temperature and agitated by shaking or stirring for a length of time sufficient to cause the reaction to occur.

For liquid phase reactions, the amount of $TaCl_5$ or $TaBr_5$ used is from 0.001 to about 5 moles, preferably 0.001 to about one mole, per mole of starting halogenated alkane, and more preferably from 0.001 to 0.250 mole and in some cases from 0.005 to 0.1 mole per mole of starting halogenated alkane. The amount of HF used in the reaction is from 1 to 30 molar equivalents per mole of halogenated alkane. The reaction can be carried out at from about 0° C. to about 185° C. The preferred temperature is about 35° C. to about 175° C. Reaction time can be from 0.5 to 18 hours; the preferred times are from 1 to 8 hours.

In the vapor phase reaction, the reactants are introduced into the reactor above their boiling points. The temperature of the reactor must also be sufficient to keep the products of the reaction in the vapro state so that they pass over into a cooled receiver beyond the reactor rather than remain in the catalyst zone for a prolonged period of time.

For vapor phase reactions, it is convenient to support the catalyst on an inert porous material such as carbon or other known supports. The amount of $TaCl_5$# or $TaBr_5$ to inert support is from 10% to 50% by weight with amounts of about 25% being preferred. The amount of HF used in the reaction is from 1 to 30 molar equivalents per mole of starting halogenated alkane. The reaction can be carried out at from about 50° C. to about 185° C. The preferred temperature is about 70° C. to about 170° C. The contact time of the reagents with the catalyst may be specified instead of reaction time. The combined operations of feed rate, control of reactor temperature and pressure and rate of removal of product from the reactor influence the residence time of the product in the reactor. It may be desirable to shorten the residence time for a given product within the reactor to control the formation of undesired products. Contact time is the average time that the reactant product mixture is in contact with the catalyst. Broadly, contact times of from 0.1 to 25 seconds are useful with preferred contact times in the range of 1 to 10 seconds.

Under the reaction conditions set forth fluorination, so that a portion of the $TaCl_5$ or $TaBr_5$ ay be in the form of $TaCl_{5-x}F_x$ or $TaBr_{5-x}F_x$. The instant invention is understood to include that condition where it may exist.

Pressure is not critical. Atmospheric, superatmospheric and autogeneous pressures are the most convenient and are therefore preferred.

The fluorinated alkanes produced by the invention have utility as refrigerants, solvents and blowing agents.

EXAMPLES

General Experimental Procedure

The reactor consisted of a 100 ml high pressure cylinder made of monel or "Inconel" containing a magnetic stirrer and an internal thermocouple. Mounted on top of the reactor was a condenser and a back pressure regulator connected to and exit lines were also present to allow for admission of reactants and withdrawal of products.

To the reactor was charged the $TaCl_5$ in the desired amount. The reactor was then cooled and evacuated. The halogenated alkane starting material and the required amount of HF was then admitted to the reactor. It was then pressurized with nitrogen to the desired pressure while still cold and then gradually brought to the desired operating temperature with stirring by using external heat provided with an oil bath. The back pressure regulator was set to the desired operating pressure prior to heating the reactor.

At the completion of the reaction, the product was isolated by conventional means and analyzed by gas chromatography. All the percentages reported in the Examples are area percent.

EXAMPLE 1

The General Experimental Procedure was followed using 20.25 g of pentachloroethane, 4.0 g of tantalum pentachloride and 15 g of anhydrous HF. The reactor was pressurized to 200 psig with nitrogen when cold and the back pressure regulator was set for 500 psig. The contents were heated with stirring at an internal temperature of 142°-144° C. for about one hour. Analysis indicated 76.9% $CF_3CHCl_2$ and 21.3° $CClF_2CHCl_2$ as the major products.

EXAMPLE 2

The General Experimental Procedure was followed using 16.8 g of 1,1,1,2-tetrachloroethane, 4.0 g of tantalum pentachloride and 6 g of anhydrous HF. The reactor was pressurized to 200 psig with nitrogen when cold and the back pressure regulator was set for 500 psig. The contents were heated with stirring at 75°-80° C. for 45 minutes. Analysis indicated 16.6% $CF_3CH_2Cl$ and 72.3% $CClF_2CH_2Cl$ as the major products.

EXAMPLE 3

Example 2 was repeated with the exception that 0.5 9 of tantalum pentachloride was used and the back pressure regulator was set for 250 psig. The contents were heated with stirring at 60°-65° C. for 90 minutes. Analysis indicated 4.6% $CF_3CH_2Cl$, 75.1% $CClF_2CH_2Cl$, 15.7% $CCl_2FCH_2Cl$ and 3.9% unreacted starting material in addition to small amounts of other organics.

EXAMPLE 4

The General Experimental Procedure was followed using 34 g of 1,1,1-trichloroethane, 0.2 g of tantalum pentachloride and 5 g of anhydrous HF. The reactor was pressurized to 50 psig with nitrogen when cold and the back pressure regulator was set at 100 psig. The contents were heated with stirring at 36°-38° C. for about two hours. Analysis indicated 7.9% $CH_3CClF_2$ 32.5% $CH_3CCl_2F$ and unreacted starting material.

EXAMPLE 5

The General Experimental Procedure was followed using 20.4 g of $CClF_2CCl_3$, 3.0 g of tantalum pentachloride and 10 g of anhydrous HF. The reactor was pressurized to 200 psig with nitrogen when cold and the back pressure regulator was set for 400 psig. contents were heated with stirring at 120°-130° C. for two hours. Product analysis indicated 96.4% $CClF_2CCl_2F$ and 2.5% unreacted starting material and small amounts of other organics.

EXAMPLE 6

Example 5 was repeated except that $CCl_2FCCl_2F$ was used as the starting material. Product analysis indicated 80.6% $CClF_2CCl_2F$ and 18.6% starting material in addition to small amounts of other organics.

EXAMPLE 7

The General Experimental Procedure was followed using 18.6 g of $CF_3CCl_3$, 3.0 g of tantalum pentachloride and 10 g anhydrous HF. The reactor was pressurized to 200 psig with nitrogen when cold and the back pressure regulator was set for 400 psig. The contents were heated with stirring at 128°-133° C. for about two hours. Product analysis indicated 37% $CF_3CCl_2F$ in addition to essentially unreacted starting material.

EXAMPLE 8

The General Experimental Procedure was followed using 30.8 g of carbon tetrachloride, 3.0 g of tantalum pentachloride and 10 9 of anhydrous HF. The reactor was pressurized to 200 psig with nitrogen when cold and the back pressure regulator was set for 500 psig.

The contents were heated with stirring at 53°–57° C. for about one hour. At the end of this period, off gas analysis indicated >96% $CCl_2F_2$. The reactor pressure was carefully vented to remove $CCl_2F_2$. The organic product from the reactor after the $CCl_2F_2$ was vented weighed 4.2 g. Analysis of this product showed 1.1% $CCl_2F_2$, 96.6% $CCl_3F$ and 2.8% carbon tetrachloride in addition to small amounts of other organics.

EXAMPLE 9

Example 8 was substantially repeated except 23.6 g of chloroform was used as the starting halogenated alkane. The contents were stirred and heated at 63°–65° C. for about one hour. Off gas analysis indicated >95% $CHClF_2$. The reactor pressure was vented to remove most of the $CHClF_2$ and the liquid organic product remaining in the reactor (7.5 g) was analyzed and found to contain 10.3% $CHClF_2$, 40.8% $CHCl_2F$ and 46.9% chloroform in addition to small amounts of other organics.

What is claimed:

1. A process for the preparation of fluorinated alkanes which comprises contacting, at a temperature of about 0° C. to about 185° C., under substantially anhydrous conditions, one molar equivalent of a starting material selected from halogenated alkanes of the following formulas

$R^1R^2R^3R^4$ C and $R^5R^6R^7R^8$C wherein $R^1$, $R^2$, $R^3$, $R^4$, are $C_zZ_{2x+1}$, wherein Z is H, F, Br, or Cl and x=0 to 10 with the proviso that at least one of $R^1$, $R^2$, $R^3$, or $R^4$ be Cl or Br or contain Cl or Br; $R^5$ and $R^6$ taken together are —$(CH_2)_n$ wherein n is an integer from 2 to 7, wherein $R^7$ and $R^8$ are $C_xZ_{2x+1}$, wherein Z is H, F, Br, or Cl and x=0 to 10, with the proviso that at least $R^7$ or $R^8$ is Cl or Br or contains Cl or Br, with HF in the presence of at least one catalyst consisting essentially of tantalum pentachloride or tantalum pentabromide to produce reaction products; removing said reaction products from contact with said catalyst and isolating a fluorinated alkane having one or more fluorine atoms above the number present in said starting material.

2. The process of claim 1 wherein the amount of HF is 1 to 30 molar equivalents.

3. The process of claim 1 wherein the catalyst is present in an amount of 0.001 to 0.250 molar equivalent.

4. The process of claim 1 wherein the catalyst is tantalum pentachloride.

5. The process of claim 1 wherein the temperature is about 35° C. to about 175° C.

6. The process of claim 1 wherein at least one of $R^1$, $R^2$, $R^3$ or $R^4$ is H.

7. The process of claim 1 wherein the halogenated alkane is selected from $CHCl_3$, $CH_2Cl_2$, $CHCl_2CHCl_2$, $CH_2ClCCl_3$, $CCl_2FCH_2Cl$, $CClF_2CH_2Cl$, $CF_3CHCl_2$, $CHClF_2$ and $CHCl_2F$.

8. The process of claim 1 wherein the catalyst is present in an amount of 0.001 to about 5 molar equivalents.

* * * * *